United States Patent [19]

McLaughlin et al.

[11] Patent Number: 5,229,419

[45] Date of Patent: Jul. 20, 1993

[54] CHEMOTHERAPEUTICALLY ACTIVE ACETOGENINS

[75] Inventors: Jerry L. McLaughlin; Yu-Hua Hui, both of W. Lafayette, Ind.

[73] Assignee: Purdue Research Foundation, West Lafayette, Ind.

[21] Appl. No.: 953,759

[22] Filed: Sep. 29, 1992

Related U.S. Application Data

[63] Continuation of Ser. No. 336,233, Apr. 11, 1989, abandoned.

[51] Int. Cl.$^5$ .................. A61K 31/365; C07D 307/12
[52] U.S. Cl. ................................. 514/473; 549/323; 549/320; 514/908
[58] Field of Search ............... 549/320, 326; 514/423, 514/908

[56] References Cited

U.S. PATENT DOCUMENTS 4,689,232 8/1987 Moeschler et al. ............. 424/195.1
4,721,727 1/1988 Mikolajczak et al. ............. 549/320
4,855,319 8/1989 Mikolajczak et al. ............. 549/320

OTHER PUBLICATIONS

Pettit, et al., Heterocycles, "Isolation and structure of Rolliniastatin 2," 28(1), pp. 213-217 (1989).
Jolad, et al., "Uvaricin, A New Antitumor Agent from Uvaria accuminata (Annonaceae)", (1982), J. Org. Chem., 47: 3151-3153.
Jolad, et al., "Desacetyluvaricin from Uvaria accuminata, Configuration of Uvaricin at C-36", (1985), J. Nat. Prod., 48: 644-645.
Dabrah and Sneden, "Rollinicin and Isorollinicin, Cytotoxic Acetogenins from Rollinia Papiilonella", (1984), Phytochemistry, 23: 2013-2106.
Etse and Waterman, "Chemistry in the Annonaceae, XXII. [4-Hydroxy-25-Desoxyrollinicin from the Stem Bark of Annona reticulata" (1984), J. Nat. Prod. 49: 684-686.
Dabrah and Sneden, "Rollinone, A New Cytotoxic Acetogenin from Rollinia papilionella", (1984), J. Nat. Prod., 47: 652-657.
Rupprecht, et al., "Asimicin, A New Cytotoxic and Pesticidal Acetogenin from the Paw Paw, Asimina triloba (Annonaceae)," (1986), Heterocycles 24: 1197-1201.
Pettit et al., "Isolation and Structure of rolliniastatin 1 from the South American tree Rollinia mucosa", (1987) Can. J. Chem., 65: 1433-1435.
Hoye, et al., "On the stereochemistry of the bistetrahydrofuranyl Moiety of Uvaricin: Proton Chemical Shifts Can Play A Crucial Role in Complex Structure Determination", (1987), J. Am. Chem. Soc., 109: 4402-4403.
Hoye and Zhuang, "Validation of the $^1$H NMR Chemical Shift Method for Determination of Stereochemistry in the Bis(tetrahydrofuranyl) Moiety of Uvaricin-related Acetogenins from Annonaceae: Rolliniastatin 1 (and (Asimicin)", (1988), J. Org. Chem., 53: 5578-5580.
Fujimoto, et al., "Squamocin, A New Cytotoxic Bis--tetrahydrofuran Containing Acetogenin from Annona squamosa", (1988), Chem. Pharm. Bull., 36: 4802-4806.
McCloud, et al., "Annonain, A Novel, Biologically Active Polyketide from Annona densicoma" Experientia, (1987), Experientia, 43: 947-949.
Alkofahi, et al., "Goniothalamicin and annonacin: Bioactive Acetogenins from Goniothalamus giganteus (Annonaceae)", (1988), Experientia, 44: 83-85.

Primary Examiner—Richard L. Raymond
Assistant Examiner—Mark W. Russell
Attorney, Agent, or Firm—Barnes & Thornburg

[57] ABSTRACT

Screening of crude extracts of the bark of Annona bullata Rich. (Annonaceae) showed cytotoxic and pesticidal activities. By monitoring with brine shrimp lethality, two novel extremely potent acetogenins, bullatacin (1) and bullatacinone (2), were isolated. Spectral and chemical methods identified bullatacin as a diastereomer of asimicin. Bullatacinone represents bullatacin with the lactone cleaved and reformed at the 4-OH. Unlike asimicin, which is more generally cytotoxic, 1 and 2 show some selective cytotoxicities in human tumor cell lines, and certain susceptible cells give ED$_{50}$ values as low as $10^{-12}$-$10^{-15}$ mcg/ml. Bullatacin was pesticidal at concentration as low as 1 ppm, while bullatacinone lacked pesticidal activities.

9 Claims, No Drawings

CHEMOTHERAPEUTICALLY ACTIVE ACETOGENINS

This is a continuation of Ser. No. 07/336,233 filed on Apr. 11, 1989, now abandoned.

BACKGROUND OF INVENTION

This invention relates to two acetogenin compounds isolated in substantially pure form from *Annona bullata* Rich. (Annonaceae). The new compounds, designated herein as bullatacin and bullatacinone, have been found to exhibit antitumor and pesticidal activity.

DESCRIPTION OF PRIOR ART

Bis(tetrahydrofuranoid) fatty acid lactones, represented by the structural formula,

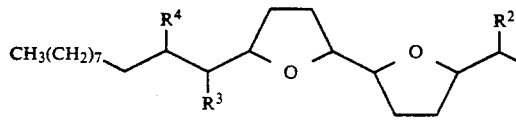

have been reported in the literature as having cytotoxic and antitumor activity. The first such compound reported [Jolad, et al., *J. Org. Chem*, 47: 3151-3153 (1982)] was called uvaricin and was characterized by an —OH group in the $R^2$ position and an acetoxy group in the $R^3$ position, with $R^1$ and $R^4$ being hydrogen. Uvaricin was isolated from the roots of *Uvaria accuminata* of the family Annonaceae and demonstrated activity in vivo against P-388 (PS) lymphocytic leukemia in mice. Subsequently, Jolad et al. [J. Nat. Prod., 48: 644–645 (1985)] disclosed the compound desacetyluvaricin which differs from uvaricin in having an hydroxyl in the $R^3$ position. Dabrah and Sneden [Phytochemistry 23: 2013-2016 (1984)] showed the isolation of the undefined stereoisomers, rollinicin, and isorollinicin from the roots of *Rollinia papilionella* (Annonaceae). These compounds were reported as having —OH in $R^2$, $R^3$ and $R^4$ positions with $R^1$ being hydrogen. Both of these compounds exhibited in vitro cytotoxicity against the P-388 lymphocytic leukemia. Etse and Waterman *J. Nat. Proc.*, 684–686 (1984)] reported the isolation and structure of 14-hydroxy 25-desoxyrollinicin which differs from rollinicin in having an hydroxyl in $R^1$ and a hydrogen in $R^4$. There is no report for the bioactivity of this compound. Dabrah and Sneden [*J. Nat. Prod.*, 47: 652-657 (1984)] disclosed another member of the series referred to as rollinone. Rollinone is characterized by a keto group at the $R^1$ carbon, hydroxyls at $R^2$ and $R^3$, and hydrogen for $R^4$ with a saturated lactone ring as illustrated in structure IA:

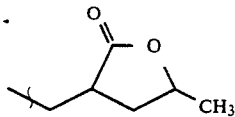

Rollinone demonstrated both cytotoxicity against P-388 in vitro and also activity in vivo against the same system in mice. The compounds having the general structure designed by Formula I, above, have acquired the name "linear acetogenins".

Cortes et al. [*Tetrahedron Lett.* 25: 3199-3202 (1984)] described two additional linear acetogenins from *Annona cherimolia* (Annonaceae), wherein the structures are reported as follows:

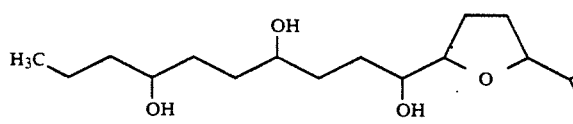

CHERIMOLINE

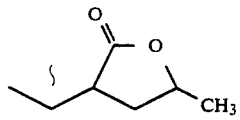

DIHYDROCHERIMOLINE

These compounds have antimicrobial activity as demonstrated against Gram negative bacteria and *Candida*.

Rupprecht et al. [*Heterocycles* 24: 1197-1201 (1986)] and Mikolajczak et al., U.S. Pat. No. 4,721,727, disclosed a new member of this series referred to as asimicin. Asimicin was isolated from *Asimina triloba* Dunal. (Annonaceae) and is characterized by two hydroxyl groups in the $R^2$ and $R^3$ positions, two hydrogens in the $R^1$ and $R^4$ positions and a hydroxyl group at carbon 4, found for the first time for this type of compound, as illustrated in partial structure (IB).

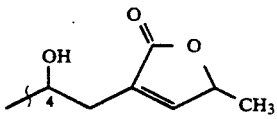

Asimicin was toxic to mice at 6.25 mg/kg and active (124% T/C at 0.0125 mg/kg) in the 3PS lymphocytic leukemia system and possesses cytotoxicities in the 9KB (human nasopharyngeal carcinoma, $ED_{50} < 10^{-5}$ µg/ml) and the 9PS (murine lymphocytic leukemia, $ED_{50} < 10^{-7}$ µg/ml systems. Promising pesticidal activity against the stripped cucumber beetle, Mexican bean beetle, mosquito larvae, blow fly larvae, melon aphid, two spotted spider mites, and the free-living nematode, *Caenorabditis elegans,* was demonstrated and this pesticidal use of the acetogenins was patented on Jan. 26, 1988 [Mikolajczak et al., U.S. Pat. No. 4,721,727]. An uncharacterized pesticidal substance called annonin and a process for its isolation from the seeds of *Annona souamosa* (Annonaceae) has been patented by Moeschler et al. [U.S. Pat. No. 4,689,232].

Pettit et al. (*Can. J. Chem.,* 65: 1433–1435 (1987)] isolated a diastereomer of asimicin from *Rollinia mucosa* (Annonaceae). This diastereomer is called rolliniastatin. Its stereochemistry, which was revealed by the first X-ray crystallographic analysis of this type of compound, is threo, cis, threo, cis, erythro, 4S and 36S and differed from asimicin which is threo, trans, threo, trans, and threo as analyzed by the $^1$H nmr analysis method developed by Hoye et al. [*J. Am. Chem. Soc.,* 109: 4402–4403(1987)]. *Rollinia mucosa* has been known in primitive medical practices of Indonesia and the West Indies as a treatment for tumors. Biological evaluation of rolliniastatin showed PS activities: 28% life extension and $ED_{50}4.5\times10^{-5}$ μg/m in cell culture.

SUMMARY OF THE INVENTION

During the screening of plants in our laboratory, we have unexpectedly discovered that *Annona bullata* Rich. in the Annonaceae family has noteworthy activities in the BST (brine shrimp lethality test), PD (crown gall antitumor activity on potato discs), 9PS (murine leukemia cytotoxicity), 9KB (human nasopharyngeal carcinoma cytotoxicity), and 9ASK (astrocytoma reversal) bioassays. In addition, activities in several pesticidal tests at Eli Lilly showed promise. The compounds found to correspond to these activities as well as selective antitumor activities were the class of natural bistetrahydrofuranoid fatty acid lactones called acetogenins. The substantially pure compounds in accordance with this invention, bullatacin and bullatacinone, have been characterized to be two new members of this unusual class of compounds. Both of these compounds have the same stereochemistry at their corresponding tetrahydrofuran rings and the two adjacent hydroxyl groups. Bullatacin is characterized by a hydroxyl group on carbon 4 and a terminal α, β-unsaturated lactone ring. Bullatacinone is characterized by a terminal methyl ketone and a lactone ring formed with a carbon 4 hydroxyl group. The structural formulas of the present compounds are illustrated below as (1) and (2).

It is an object of this invention to provide the two Annonaceous acetogenin compounds designated as bullatacin and bullatacinone in substantially pure form.

It is also an object of this invention to provide two of the most active acetogenins known today in in vitro human tumor cell lines.

It is still a further object of this invention to provide a method for converting bullatacin to bullatacinone, bullatacinone exhibiting a more selective antitumor activity.

It is a further object of the invention to provide bullatacin as a new and potent pesticide in the acetogenin group.

Other objects and advantages of the invention will become readily apparent from the ensuing description.

DETAILED DESCRIPTION OF THE INVENTION

The starting material for use in the invention is the bark of *Annona bullata* Rich. (Annonaceae), and it is considered likely, by the screening of other parts of the plant, that other tissues such as twigs, wood, roots, seeds and leaves would also contain extractable quantities of the subject compounds.

The bark material is prepared for extraction by grinding in a conventional mill to a suitable particle size, usually in the range of about 0.001–3 mm. in diameter, and more preferably in the range of 0.1–2 mm. The ground material is extracted by percolating with 95% EtOH. The ethanol solubles are concentrated to remove the bulk of the solvent, at least to the point of reducing the extract to a thick syrup. The resultant concentrate is partitioned between water and a water-immiscible solvent, such as chloroform, in order to remove the water solubles which are freeze dried and labelled F002. The chloroform solubles are recovered as a syrup residue using a solvent evaporator and labelled as F003. The insoluble interface was dried at ambient temperature and labelled F004. F003 then is partitioned between hexane and 90% aqueous MeOH in order to remove hexane solubles which are vacuum dried and labelled as F006. The 90% aqueous MeOH solubles are recovered by vacuum evaporation to a thick syrup as a crude acetogenin-containing extract F005.

Separation and purification of pure acetogenins from the crude extract (F005) can be affected by the use of the proper combination of conventional techniques including, for example, column chromatography (CC), thin-layer chromatography (TLC), medium-pressure chromatography (MPC) and chromatotrons. While not desiring to be limited thereto, the details of the separation procedure are illustrated by the following examples. Fractionation of the ethanolic extract was guided by assay with the brine shrimp lethality test (BST) and confirmed by assays on tumor cell cultures. Pesticidal tests were conducted at Eli Lilly Laboratories (Greenfield) in indicator organisms following standard procedures.

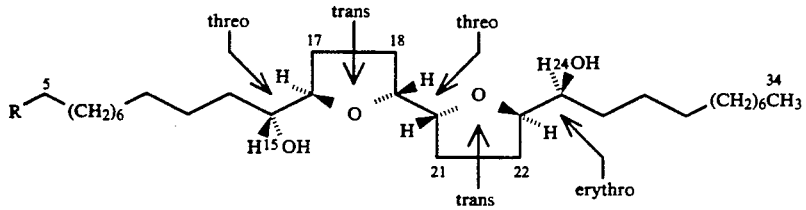

EXAMPLES

Bioassay Procedure

The following bioassays were used to guide the phytochemical fractionation described below.

The extracts, fractions, and isolated compounds were routinely evaluated for lethality to brine shrimp larvae (BST). The $LC_{50}$ of brine shrimp (*Artemia salina* Leach) was determined by substantially the same method described by Meyer et al. [*Planta Med.*, 45: 31–34 (1982)]. The test sample was dissolved in solvent and added to 2-dram vials in an amount to provide 1000, 100, 10, 1, etc. p.p.m. of material in the final brine preparation, assuming complete miscibility in the brine. The vials were dried in vacuo, and artificial sea water, prepared from a commercial salt mixture, was added. Ten brine shrimp larva (nauplii), 48–72 hrs. old, were introduced to the vial, and the volume was made up to 5 ml. with the sea water. After 24 hrs., the percent mortality was computed. Subsequently, $LC_{50}$ values and 95% confidence limits were calculated by a Finney probit analysis to permit comparison of potencies of extracts and fractions.

Occasional checks in the potato disc (PD) assay assured us that antitumor activity was present [Ferrigni et al., *J. Nat. Prod.*, 45; 679–686 (1982)]. Cytotoxicity tests were performed at the Purdue Cell Culture Laboratory, Purdue Cancer Center, using standard protocols for 9KB (human nasopharyngeal carcinoma) and 9PS (a chemically-induced murine lymphocytic leukemia) [Suffness et al., *Methods In Cancer Research*. Vol. 16: 73 (1979), V. T. DeVita, Jr. and H. Busch eds., Academic Press, New York], 9ASK (astrocytoma reversal) [Lgarashi et al., *Cell Struct. and Funct.*, 3: 107 (1978)], A-549 (human lung carcinoma) [Giard et al., *J. Nat. Cancer Inst.*, 51: 1417–1423 (1973)], and HT-29 (human colon adenocarcinoma) [Fogh J. (ed.), Human Tumor Cells, In Vitro, Plenum Press, New York: 115–159 (1975)].

Isolated pure compounds were sent to the National Institute of Health, National Cancer Institute, Bethesda, Md., for testing in human cancer cell line panels including leukemia, non-small cell lung cancer, small cell lung cancer, CNS cancer, melanoma, ovarian cancer and renal cancer.

Pesticidal bioassays were conducted at Eli Lilly Laboratories (Greenfield, Ind.) following standard procedures with eight indicator organisms: mosquito larvae (ML) *Aedes aegypti* (in the media), blowfly larvae (BFL) (1% in the diet), corn root worm (CRW) *Diabrotics undecimcuntata howardii* (in soil), two-spotted spider mite (2SSM) *Tetranychus urticae* (on foliage), southern army worm (SAW) *Spodoptera eridania* (on foliage), melon aphid (MA) (5000 ppm on foliage), cotton aphid (CA) *Aphis gossypii*, (on foliage) and *Haemonchus contortus* (HC) (a nematode, 0.1% in the media).

Isolation of the Compounds

A. Extraction Procedures

Approximately 3.9 kg of *Annona bullata* Rich. (Annonaceae) bark (M-06983, PL-103519) was collected by Edward Garvey at the USDA Subtropical Horticulture Research Station, ARS, 13601 Old Culture Rd., Miami, Fla. 33158. The tree originated from seeds collected in Cuba in 1933 by Robert M. Grey of Harvard University. Air-dried bark was pulverized through a 2 mm screen in a Wiley mill. The pulverized bark was extracted by exhaustive percolation with 777 liters of 95% EtOH. Vacuum evaporation left 380 g of syrupy residue (F001). F001 was partitioned between $CHCl_3H_2O$ (1:1), and the water solubles were freeze dried and labelled F002 (11 g). The chloroform solubles were vacuum evaporated to form F003 (181 g). The insoluble interface was air dried and labelled F004 (188 g). Then F003 was partitioned between hexane/90% aqueous MeOH (1:1). The 90% MeOH fraction was vacuum evaporated to a thick syrup and labelled F005 156 g.) The hexane residue (25 g) was labelled F006. The bioassay data (Table 1) clearly showed that the most activity was concentrated in the 90% MeOH fraction (F005).

TABLE 1

Bioactivities of Initial Fractions from *Annona bullata* Rich.

| | BST $LC_{50}$ mcg/ml 95% Confidence Interval | PD % Inhibition | 9KB $ED_{50}$ mcg/ml | 9PS $ED_{50}$ mcg/ml | 9ASK reversal | Protein kinase C % Displacement 100 mcg/ml |
|---|---|---|---|---|---|---|
| F001 | 0.0062 0.0120 ↓ 0.0009 | —[a] | 20 | $<10^{-2}$ | not active | 11% |
| F002 | >100 | — | >10 | >10 | — | — |
| F003 | 0.0030 0.0036 ↓ 0.0010 | — | $10^{-1}$–$10^{-2}$ | $<10^{-2}$ | not active | 67% |
| F004 | 5.4000 838→1.53 | — | >10 | 2.11 | — | — |
| F005 | 0.0025 0.0050 ↓ 0.0001 | 78% | $<10^{-5}$ | $<10^{-2}$ | slight active | 68% |
| F006 | >100 | — | >10 | 4.10 | — | — |

[a] A dash (-) indicates that tests were not conducted.

B. Chromatographic Separations

F005 (80 g) was absorbed onto 100 g of Celite and applied to a column of Si gel (3 kg) packed in a slurry of hexane. A gradient of hexane—$CHCl_3$—MeOH was used to elute the column, collecting 82 fractions of 100–200 ml each. Fractions were combined into pools according to their similar TLC patterns [$CHCl_3$—MeOH (9:1) on Si gel, phosphomolybdic acid spray], weighed, and bioassayed by the BST.

The largest and the most toxic pool (P40-51, 25 g) was absorbed onto 100 g of Celite and chromatographed over a column of 4.4 kg of Si gel packed as a slurry in $CHCl_3$. A gradient of $CHCl_3$—EtOAc—MeOH was used to elute the column, collecting fractions of 100–200 ml. Pools were made after TLC and bioassayed in the BST. From the most toxic pool (P106-111), which had been eluted with CHCl$_3$—EtOAc (1:1), a white precipitate was obtained. Recrystallization from EtOAc gave fine white needles which were labelled as bullatacin (1) (100 mg); this material was homogeneous in several TLC systems. From P17-40, which had been eluted with CHCl$_3$, another white precipitate appeared which was recrystallized from EtOAc to a white homogeneous solid (5 mg), later designated bullatacinone (2).

Pool 31-39, from the first column, stood for some time. Orange crystals formed and were recrystallized from MeOH to yield yellow needles (150 mg); this material was identified (mp, ir, ci and eims) as liriodenine [Lopez et al. *Rev. Cubana Farm.*, 20: 83-86 (1986) (Span.)]. The residue (5.7 g) of the mother liquor was chromatographed over Si gel at medium pressure in a Michel-Miller column, eluted with a gradient of CHCl$_3$—MeOH. A white solid formed in pool 104-113; this was recrystallized from EtOAc to yield fine white needles (8 mg) of additional bullatacinone (2).

Upon standing, pool 8-17 from the first chromatography column gave large colorless crystals. After recrystallization from MeOH, these were identified (uv, ei and cims, hrms, $^1$H and $^{13}$C nmr) as (−)-kaur-16-en-19-oic acid [Leboeuf et al., *Phytochemistry*, 21: 2783-2813 (1982)].

Characterization of Compound Structures

A. Structural Characterization of Bullatacin (1)

Mp 69-70°; $[\alpha]23°/589 = +13.00$, $[\alpha]23°/578 = +14.70$, $[\alpha]23°/546 = +19.04$, $[\alpha]23°/436 = +36.63$, $[\alpha]23°/365 = +66.99$ (c, 0.004, CHCl$_3$); cims (isobutane) m/z 623 (MH$^+$), cims (ammonia) m/z 622 (M+NH$^+_4$—H$_2$O), 640 (M+NH$^+_4$), eims m/z 622 (M$^+$); hr cims 623.4847 (calc. 623.4889) for C$_{37}$H$_{66}$O$_7$; uv (EtOH) λ max 215.5 nm (ε=7974); ir (KBr) cm$^{-1}$ 3430 (hydroxyl), 1750 (carbonyl).

These spectral characteristics indicated that 1 belongs to the familiar class of bioactive bistetrahydrofuran acetogenins which contain 37 carbons and two long hydrocarbon chains, one of which terminates with a γ-lactone.

The structure of fragment A, which contains the lactone ring and one of the three hydroxyl groups, was elucidated by high field $^1$H nmr (Table 2), $^{13}$C nmr (Table 3), and ms spectral analyses.

TABLE 2

| | $^1$H NMR Assignments and Comparisons of Compounds.* | | |
|---|---|---|---|
| | Bullaticin (1) 470 MHz, CDCl$_3$ | Bullatacin (1) 470 MHz, C$_6$D$_6$ | Bullatacinone (2) 470 MHz, C$_6$D$_6$ |
| 2 | — | — | 2.71dddd2, 3a(9.34) 2, 3b(9.34) 2, 35b(3.42) 2, 35a(9.34) |
| 3a | 2.50 dddd 3a, 3b(15.0) 3a, 4 (4.0) 3a, 35(1.5) 3a, 36(1.1) | 2.30 dddd 3a, 3b(15.0) 3a, 4 (4.0) 3a, 35(1.5) 3a, 36(1.1) | 1.70ddd 3a, 3b(12.82) 3a, 4 (3.38) 3a, 2 (9.34) |
| 3b | 2.36 ddt 3b, 3a(15.0) 3b, 4 (8.0) 3b, 35(1.4) | 2.20 ddt 3b, 3a(15.0) 3b, 4(8.0) 3b, 35(1.4) | 1.40ddd |
| 4 | 3.80m | 3.71br tt | 4.05m |
| 5 | 1.3-2.0 | 1.3-2.1 | 2.3-2.0 |
| 6-13 | 1.25br s | 1.25br s | 1.25br s |
| 14 | 1.35m | 1.3-2.1 | 1.40, 1.55 |
| 15 | 3.38tt 15, 16 (8.0) 15, 14 (2.0) | 3.45ttt 15, 16 (8.0) 15, 14 (2.0) 15, 17 (1.0) | 3.49tt 15, 16 (8.06) 15, 14 (2.38) |
| 16 | 3.83m | 3.85ddd 16, 17a(8.0) 16, 17b(6.9) 15, 17 (1.0) | 3.85ddd 16, 17a(8.06) 16, 17b(6.96) |
| 17, 18 | 1.3-2.0 | 1.3-2.1 | 1.65, 1.35 |
| 19x | 3.92m | 3.89m | 3.89m |
| 20x | 3.83m | 3.67ddd 20, 21a(6.0) 20, 21b(1.0) 20, 19(15.0) | 3.66ddd 20, 21a(5.96) 20, 21b(1.00) 20, 19(14.93) |
| 21, 22 | 1.3-2.0 | 1.3-2.1 | 1.52, 1.42 |
| 23y | 3.92m | 3.99dt 23, 24(8.5) 23, 22(2.5) | 3.95dd 23, 24(8.4) 23, 22(2.5) |
| 24y | 3.83m | 3.89m | 3.89m |
| 25 | 1.3-2.0 | 1.3-2.1 | 2.10, 1.60 |
| 26-33 | 1.25br s | 1.25br s | 1.25br s |
| 34 | 0.85t 34, 33(6.81) | 0.9t 34, 33(6.81) | 0.90t 34, 3 (7.05) |
| 35a | | | 1.93dd 35a, 35b(18.31) 35a, 2 (9.34) |
| 35b | 7.17d 35, 36(1.70) | 6.25d 35, 36(1.70) | 2.53dd 35b, 2 (3.42) |
| 36 | 5.05ddq 36, 37(6.83) | 4.12ddq 36, 37(6.83) | — |
| 37 | 1.41d | 0.80d | 1.55s |

| | Rolliastatin 300 MHz, CDCl$_3$ | Asimicin 470 MHz, CDl$_3$ | Asimicin 470 MHz, C$_6$D$_6$ |
|---|---|---|---|
| 2 | — | — | — |
| 3a | 2.50 dddd 3a, 3b(15.1) 3a, 4 (3.5) 3a, 35(1.5) 3a, 36(1.6) | 2.51 dddd 3a, 3b(15) 3a, 4 (3.5) 3a, 35(1.5) 3a, 36(1.7) | 2.35 |
| 3b | 2.36 dddd 3b, 4 (8.1) 3b, 35(1.2) | 2.38ddt 3b, 4 (8.0) 3b, 35(1.5) 3b, 36(1.5) | 2.27 |

TABLE 2-continued

| | 3b, 36(1.5 | | |
|---|---|---|---|
| 4 | 3.85m | 3.86m | 3.77 |
| 5 | 1.45 | 1.55m | 1.4–1.5 |
| 6–13 | 1.25 | 1.25m | 1.35 |
| 14 | 1.50m | 1.55m | 1.55 |
| 15 | 3.38m | 3.37br, q | 3.45 |
| 16 | 3.85m | 3.79–3.85m | 3.86 |
| 17, 18 | 1.7–1.9m | 1.6–2.0m | 1.4–1.8 |
| 19, 20 | 3.85m | 3.79–3.89m | 3.73 |
| 21, 22 | 1.7–1.9m | 1.6–2.0m | 1.4–1.8 |
| 23, 24 | 3.85m | 3.79–3.89m(23) | 3.86(23) |
| | | 3.37br, q (24) | 3.45(24) |
| 25 | 1.45m | 1.55m | 1.55 |
| 26–33 | 1.25br, s | 1.25m | 1.35 |
| 34 | 0.85t | 0.86t | 0.90 |
| 35 | 7.16ddd | 7.17q | 6.35 |
| 36 | 5.02dddq | 5.06qq | 4.3 |
| 37 | 1.40d | 1.41d | 0.86 |

*Some coupling constants were obtained by decoupling experiments
x, y Indicate that assignments may be interchangable

TABLE 3

$^{13}$C NMR (CDCl$_3$) Assignments and Comparisons.$^a$

| Carbon No. | Bullatacin (50 MHz)(1) | Bullatacinone (50 MNz)(2) | Rolliniastatin | Asimicin |
|---|---|---|---|---|
| 1 | 174.51s | 178.73s | 174.5s | 174.6s |
| 2 | 131.11s | 44.18d | 131.1s | 131.1s |
| 3$^a$ | 33.23t | 34.41t | 33.2t | 33.4t |
| 4 | 69.91d | 78.86d | 69.9d | 69.9d |
| 5$^a$ | 37.34t | 36.67t | 37.4t | 37.5t |
| 6$^a$ | 25.99t | 25.99t | 26.0t | 25.6t |
| 7–12$^a$ | 29.92t | 29.56t | 29.5t | 29.6t |
| | 29.28t | 29.37t | 29.3t | 29.3t |
| 13$^a$ | 25.54t | 25.22t | 25.7t | 25.6t |
| 14$^a$ | 33.23t | 33.19t | 34.1t | 33.6t |
| 15 | 74.08d | 74.10d | 74.0d | 74.1d |
| 16 | 83.20d | 83.26d | 83.0d | 83.1d |
| 17$^a$ | 28.91t | 28.92t | 28.7t | 28.4t |
| 18$^a$ | 28.37t | 28.37t | 27.8t | 28.4t |
| 19 | 82.44d | 82.44d | 81.1d | 81.7d |
| 20 | 82.17d | 82.19d | 81.0d | 81.7d |
| 21$^a$ | 28.91t | 28.92t | 27.8t | 28.4t |
| 22$^a$ | 28.37t | 28.37t | 28.4t | 28.4t |
| 23 | 82.75d | 82.77d | 83.0d | 82.8d |
| 24 | 72.34d | 71.26d | 71.8d | 74.1d |
| 25$^a$ | 32.38t | 32.37t | 32.8t | 33.4t |
| 26$^a$ | 25.54t | 25.59t | 25.5t | 25.6t |
| 27–31$^a$ | 29.49t | 29.56t | 29.6t | 29.6t |
| | 29.28t | 29.25t | 31.9t | 29.3t |
| 32$^a$ | 31.83t | 31.85t | 31.9t | 31.9t |
| 33 | 22.62t | 22.63t | 22.6t | 22.7t |
| 34 | 14.10q | 14.05q | 14.1q | 14.1q |
| 35 | 151.70d | 35.42t | 151.7d | 151.6d |
| 36 | 77.88d | 205.44s | 77.9d | 77.9d |
| 37 | 19.06q | 24.46q | 19.1q | 19.1q |

$^a$Assignments of similar signals, as indicated, may be interchanged.

A positive response to Kedde's reagent, the strong ir absorption at 1750 cm$^{-1}$ and the uv absorption maximum at 215.5 nm ($\epsilon$=7974) in EtOH suggested the presence of an $\alpha,\beta$-unsaturated $\gamma$-lactone. $^1$H—$^1$H decoupling experiments between protons 3 and proton 4 in the 470 MHz ) (C$_6$D$_6$) spectrum revealed the presence of the hydroxyl group at carbon 4. Exact mass 141.0550 (calc. 141.0552) for C$_7$H$_9$O$_3$ showed the cleavage between carbon 4 and carbon 5; ms of the TMS derivative of 1 and the dihydro derivative also supported the structure of fragment A.

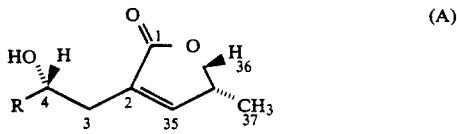

(A)

The structure of fragment B, which contains the two tetrahydrofuran rings and the remaining two hydroxyl groups, was elucidated by essentially the same techniques.

$^{13}$C Nmr (50 MHz) and $^1$H nmr resonances were directly analogous to similar signals of asimicin [Rupprecht et al., Heterocycles, 24: 1197–1201 (1986)], uvaricin [Jolad et al., J. Org. Chem., 47: 3151–3153 (1982)], and rolliniastatin [Pettit et al., Can. J. Chem., 65: 1433–1435 (1987)], indicating the common presence of a bistetrahydrofuran moiety as illustrated in fragment B. Exact mass measurement of a second peak at m/z 141.0909 (calc. 141.0916) corresponded to C$_8$H$_{13}$O$_2$. It is proposed that this peak represents cleavage between carbons 15 and 16, and between carbons 23 and 24. Eims of the TMS and acetyl derivatives of 1, $^1$H nmr of the triacetate of 1 and $^1$H—$^1$H decoupling experiments on the 470 MHz spectrometer for 1 confirmed these assignments.

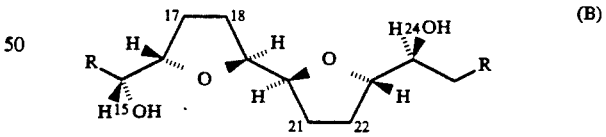

(B)

Subtracting fragments A and B, the remainder, C$_{20}$H$_{41}$, of the structure of bullatacin (1) belongs to the unsubstituted alkyl chain. This was corroborated by multiple CH$_2$ resonances between $\delta$ 1.2–1.5 in the $^1$H nmr (C$_6$D$_6$) and $\delta$ 20–40 in the $^{13}$C nmr (Tables 2 and 3). The placement of fragments A and B along the hydrocarbon chain was accomplished through analysis of the ms fragmentation pattern of 1 and its TMS, acetate, and hydrogenation derivatives.

The absolute value two dimensional homonuclear correlated spectrum (2D-COSY, 200 MHz) of bullatacin (1) confirmed the proton assignments (Table 2) and proton connectivities except for the aliphatic —CH$_2$— chain.

Surprisingly, this carbon skeleton of bullatacin (1) is the same as that of asimicin [Rupprecht et al., *Heterocycles*, 24: 1197–1201, (1986)], and rolliniastatin [Pettit et al. *Can. J. Chem.*, 65: 1433–1435, (1987). However, the mp, co-TLC, ¹H nmr, and most importantly, the bioactivities are different. The compounds are stereoisomers at one or more of their eight chiral centers. Since 1 yielded crystals which were not suitable for X-ray diffraction studies and since the acetogenins are difficult to convert into crystalline derivatives suitable for X-ray analysis [Pettit et al., *Can. J. Chem.*, 65: 1433–1435, (1987)], other methods were used to predict the stereochemistry.

First, the relative configuration of six of the eight chiral centers, those on the bistetrahydrofuran ring system and its two adjacent hydroxyl bearing carbons, was obtained by comparing the ¹H nmr (CDCl₃) spectral signals of bullatacin (1) acetate (Table 4) with those of a recently published series of synthetic dibutylated diacetate bistetrahydrofuran models and uvaricin and uvaricin acetate; stereochemical information could then be extracted from "iterative and synergistic" analysis of very small differences in the high-field proton chemical shifts [Hoye et al. *J. Am. Chem. Soc.*, 109: 4402–4403 (1987)].

threo. From X-ray data, rolliniastatin is reported to be threo, cis, threo, cis, and erythro [Pettit et al., *Can. J. Chem.*, 65: 1433–1435, (1987)].

The stereochemistry at the remaining two chiral centers, carbon 4 and carbon 36, was determined by comparing nmr spectral data with those in the literature for rolliniastatin [Pettit et al., *Can. J. Chem.*, 65: 1433–1435, (1987)]. Furthermore, essentially identical CD curves for rolliniastatin, asimicin and bullatacin suggested their stereochemical identity in this region. The CD data are given below.

Bullatacin (1) (c, 0.025, abs. EtOH); $[\theta]_{265}$, 0.00°; $[\theta]_{260}$, −298.56°; $[\theta]_{250}$, −995.20°, $[\theta]_{240}$, −2189.44°; $[\theta]_{233}$, −2587.52°; $[\theta]_{230}$, −2348.67°; $[\theta]_{225}$, 0.00°; $[\theta]_{220}$, 4378.88°; $[\theta]_{218}$, −7961.60°.

Rolliniastatin (c, 0.025; abs. EtOH); $[\theta]_{265}$, 0.00°; $[\theta]_{260}$, −199.04°; $[\theta]_{250}$, −1393.28°; $[\theta]_{240}$, −2587.52°; $[\theta]_{235}$, −2786.56°; $[\theta]_{230}$, −2089.92°; $[\theta]_{225}$, 0.00°; and $[\theta]_{220}$, 6369,28°.

Asimicin (c, 0.025; abs. EtOH); $[\theta]_{265}$, 0.00°; $[\theta]_{260}$, −199.04°; $[\theta]_{250}$, −995.20°; $[\theta]_{246}$, −2288.95°; $[\theta]_{234}$, −2687.04°; $[\theta]_{230}$, −2388.48°; $[\theta]_{225}$, −59.712°; $[\theta]_{224}$, 0.00°; $[\theta]_{220}$, 4080.32°; and $[\theta]_{218}$, 7862.08°.

From the above data, we conclude that the structure of bullatacin, with stereochemistry defined, is as illus-

TABLE 4

¹H NMR Assignments and Comparisons of Acetate Derivatives.*

| | Bullatacin triacetate (470 MHz, CDCl₃) | Bullatacinone diacetate (470 MHz, CDCl₃) | Asimicin triacetate 300 MHz, CDCl₃) | Uvaricin acetate (300 MHz, CDCl₃) |
|---|---|---|---|---|
| 2 | — | 3.02ddd 2, 3a(12.82) 2, 3b(9.34) 2, 35a(9.34) 2, 35b(3.42) | — | — |
| 3a | 2.52dddd | 1.74m | 2.53 | 2.26ddd |
| 3b | 2.58ddt | 2.00m | 2.53 | |
| 4 | 5.11dddd 4, 3a(4.0) 4, 3b(7.0) 4, 5a(10.1) 4, 5b(1.8) | 4.53dddd | 5.09 | 1.25m |
| 5 | 1.5–2.0 | 1.5–2.0 | 1.5–1.9 | 1.25m |
| 6–13 | 1.25br s | 1.25br s | 1.25 | 1.25m |
| 14 | 1.5–2.0 | 1.5–2.0 | 1.5–1.9 | 1.75–1.9 |
| 15 | 4.88dt 15, 16(8.0) 15, 14(2.0) | 4.80dt 15, 16(8.0) 15, 14(2.0) | 4.85 | 4.86ddd |
| 16 | 4.00ddd | 4.00ddd | 3.98 | 3.98ddd |
| 17, 18 | 1.5–2.0 | 1.5–2.0 | 1.5–1.9 | 1.75–1.9 |
| 19, 20 | 3.9br t | 3.9br t | 3.9 | 3.89br, t |
| 21, 22 | 1.5–2.0 | 1.5–2.0 | 1.5–1.9 | 1.75–1.9 |
| 23 | 4.00ddd | 4.00ddd | 2.98 | 3.98ddd |
| 24 | 4.93ddd 24, 25a(3.0) 24, 25b(2.8) | 4.93ddd 24, 25a(3.0) 24, 25b(2.8) | 3.83 | 4.92ddd |
| 25 | 1.5–2.0 | 1.5–2.0 | 1.5–1.9 | 1.75–1.9 |
| 26–33 | 1.28br s | 1.28br s | 1.25 | 1.25m |
| 34 | 0.89t 34, 33(7.05) | 0.89t 34, 33(7.05) | 0.87 | 0.878t |
| 35 | 7.09d 35, 36(1.29) | 2.66dd 35a, 35b(18.3) 35a, 2(9.34) 3.04dd 35b, 2(3.42) | 7.06 | 6.98qq |
| 36 | 5.02qq | — | 5.01 | 4.99dtq |
| 37 | 1.41d 36, 37(7.05) | 2.20s | 1.42 | 1.40d |
| 4 OAc | 2.04s | — | 2.01 | — |
| 15 OAc | 2.06s | 2.05s | 2.06 | 2.074s |
| 24 OAc | 2.09s | 2.08s | 2.06 | 2.046s |

*Preparation: 10 mg of parent compound is dissolved in a 1:1 mixture of acetic anhydride/pyridine and left overnight. Addition of ice water followed by extraction with chloroform yields the corresponding peracetylated derivative.

Results of bullatacin acetate nmr resonances (Table 4) suggested that the configuration of fragment B is threo, trans, threo, trans, erythro, the same as in uvaricin or erythro, trans, threo, trans, and threo. However, differences in the ¹H nmr (CDCl₃, 200 MHz) of bullatacin compared with that of uvaricin indicate the probable configuration of bullatacin to be erythro, trans, threo, trans, threo, as illustrated for 1. Similarly, we have determined that asimicin is threo, trans, threo, trans, trated as in formula 1 above.

B. Structural Characterization of Bullatacinone (2)

Mp 90.5–90.7°; $[\alpha]23°/589 = +12.00$, $[\alpha]23°/578 = +12.50$, $[\alpha]23°/546 = +14.50$, $[\alpha]23°/436 = +29.75$, $[\alpha]23°/365 = +51.25$, (c, 0.400, CHCl₃); cims (NH₃) m/z 623 (MH⁺) and 640

(MNH+4); cims (isobutane) m/z 623 (MH+) and 661 (MH+38); hr cims 623.4839 (calc. 623.4889) for $C_{37}H_{66}O_7$; eims; $^1$H nmr (Table 2); $^{13}$C nmr (Table 3).

Negative results with Kedde's reagent, weak uv end absorption at $\lambda_{max}$ 203.5 nm ($\epsilon=3799$), and ir (KBr) absorptions at 1770 and 1715 cm$^{-1}$ showed an absence of the conjugated $\alpha,\beta$-unsaturated $\lambda$-lactone ring usually found in these acetogenins.

The $^1$H nmr (Table 2) of bullatacinone (2) looked quite similar to that of 1 with an obvious presence of two tetrahydrofuran rings with adjacent hydroxyls as in fragment B of 1. To determine the stereochemistry of fragment B of 2, the diacetate of 2 was made, and the $^1$H nmr (470 MHz) (CDCl$_3$) spectrum was compared with that of the triacetate of 1 (Table 4). The comparison showed that the bistetrahydrofuran ring of 2, together with the two adjacent hydroxyl groups at carbon 15 and carbon 24, have exactly the same configuration as that of 1, i.e., erythro, trans, threo, trans, threo. The $^{13}$C nmr of 2 (Table 3) showed two carboxyl carbons and the absence of the vinyl carbon seen in 1.

The eims and cims of bullatacinone (2) and the 2-TMS derivative and exact mass measurements of selected fragments showed that the alkyl chain was the same length as in 1. The observation that the 2-TMS derivative in cims did not show the m/z 213 typical of the A fragment of 1 suggested the lack of a 4-OH. The ir spectrum of 2 at 1770 and 1715 cm$^{-1}$ suggested two carbonyl groups of which one corresponds to a saturated lactone ring. In the $^1$H nmr (470 MHz) of 2-acetate, a characteristic signal at $\delta 2.20$ (s, 3H) in CDCl$_3$ suggested a terminal methyl ketone. It seemed likely that this compound has the lactone formed with the 4-OH, leaving a carbonyl at C36. To test this proposition, 1 was converted into 2 by treating with base to hydrolyze the lactone and to recyclize upon acidification:

15 milligrams of 1 was treated with 2% KOH in t—BuOH (1 ml) at room temperature for 24 hours; the solution was acidified with 10% HCl to pH 1-2, set aside for 30 minutes, and, partitioned between CHCl$_3$/H$_2$O. The reaction product (in the CHCl$_3$ residue) showed two components (TLC), and one was identical to 2 (four TLC systems). Resolution on a microcolumn of Si gel gave 2 which was identical (co-TLC, cims and $^1$H nmr) with 2 isolated from the plant material.

To determine the absolute stereochemistry at C4, the CD curve of bullatacinone (shown below) was compared with those of rubrenolide and rubrynolide, two 2,4-disubstituted-$\gamma$-butyrolactones whose structures are shown below [Franca et al., Phytochemistry, 16: 257-262, (1977)].

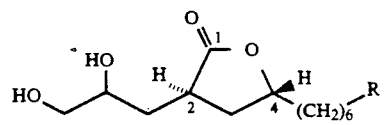

rubrenolide: R — —CH=CH$_2$
rubrynolide: R = —C≡CH

CD of bullatacinone (2): (c, 0.1, abs. EtOH); $[\theta]_{250}$, 0.00°; $[\theta]_{240}$, $-124.4°$; $[\theta]_{235}$, $-248.8°$; $[\theta]_{230}$, $-497.6°$; $[\theta]_{225}$, $-870.8°$; $[\theta]_{220}$, $-1555°$; $[\theta]_{215}$, $-1990.4°$; $[\theta]_{212}$, $-2177°$; $[\theta]_{210}$, $-1492.8°$; $[\theta]_{207}$, $-746.4°$; $[\theta]_{205}$, $-0.00°$. 2 showed a negative Cotton effect, whereas rubrenolide and rubrynolide gave positive Cotton effects. Application of the modified Hudson lactone rule [Klyne et al., J. Chem. Soc., 7237-7242, (1965)] enabled the assignment of the S-configuration to the chiral center at C4. For the stereochemistry at position 2, the $^{13}$C nmr showed three carbons (C1, C2 and C4) as doublets. This suggested that bullatacinone is a mixture of two stereoisomers at carbon 2. $^1$H Nmr confirmed this proposal. From the $^{13}$C nmr, the ratio of the two isomers at C2 was estimated to be 2:1. The phase sensitive two dimensional homonuclear correlated spectrum (2D COSY, 500 MHz) of bullatacinone confirmed the proton assignments and provided the proton proton connectivities in Table 2. From the above data, we conclude that bullatacinone is as illustrated in structure 2 partially racemized at carbon 2.

Biological Activity

A. Anticancer Activities

Anticancer activity is a potential use even for the crude extract. The bioassay results for the lethality of brine shrimp (BST), the inhibition of crown gall tumors on potato discs (PD), the reversal in morphology of db-cAMP induced AC glioma cells from that of mature, differentiated astrocytes to that of immature AC glioma cells (mouse brain cells) (9ASK), the dose that inhibits cell growth to one-half that of untreated poorly differentiated human epidermic carcinoma (9KB), the dose that inhibits cell growth to one-half that of a methylcholanthrene-induced lymphoid neoplasm in a DBA/2 mouse (9PS), and the percent displacement in a protein kinase C test for initial extract fractions are shown in Table 1. Obviously, the bioactivity is concentrated in F005.

Corresponding to these bioactivities, the pure compounds isolated from F005, bullatacin and bullatacinone, showed additional promising results (Table 5).

TABLE 5

| | Bioactivities of 1 and 2 and their derivatives | | | | |
|---|---|---|---|---|---|
| | BST LC$_{50}$, mcg/ml 95% Confidence Interval | 9PS ED$_{50}$, mcg/ml | 9KB ED$_{50}$ mcg/ml | A549 ED$_{50}$, mcg/ml | HT29 ED$_{50, mcg/ml}$ |
| Bullatacin(1) | 0.00159 0.0124 ↓ 0.0008 | $10^{-15}$–$10^{-16}$ | $6.188 \times 10^{-14}$ | $1.25 \times 10^{-13}$ | $10^{-12}$ |
| Bullatacin triacetate (1-Ac) | 5.7 17.12 ↓ 2.84 | $3.89 \times 10^{-3}$ | $6.85 \times 10^{-7}$ | $2 \times 10^{-3}$ | $>10^{-1}$ |

TABLE 5-continued

Bioactivities of 1 and 2 and their derivatives

| | BST $LC_{50}$, mcg/ml 95% Confidence Interval | 9PS $ED_{50}$, mcg/ml | 9KB $ED_{50}$ mcg/ml | A549 $ED_{50}$, mcg/ml | HT29 $ED_{50}$, mcg/ml |
|---|---|---|---|---|---|
| Dihydro-[b] bullatacin (1-H$_2$) | 0.0145 0.0300 ↓ 0.0100 | —[a] | — | $<10^{-6}$ | $3.33 \times 10^{-5}$ |
| Bullatacinone (2) | 0.0030 0.0090 ↓ 0.0000 | $4.23 \times 10^{-3}$ | $<10^{-12}$ | $10^{-3}$ | $5 \times 10^{-12}$ |
| Bullatacinone diacetate (2-Ac) | >10 | $4.22 \times 10^{-2}$ | $5 \times 10^3$ | $2.8 \times 10^{-2}$ | $10^{-1}$ |

[a] A dash (-) indicates that tests were not conducted.
[b] Obtained by hydrogenation of bullatacin in the presence of a Pd/C catalyst following standard laboratory procedures.

These two compounds are the most bioactive acetogenins reported to this date. When derivatized, such as by acetylation and hydrogenation, the bioactivities decrease as shown in Table 5. But the safety range for treatments might be larger. In this table, two cytotoxicity tests against human tumor cell lines such as the human lung carcinoma (A-549) [Giard et al., *J. Nat. Cancer Inst.* 51: 1417-1423 (1973)] and the human colon adenocarcinoma (HT-29) [Fogh, J. (ed.) Human Tumor Cells, In Vitro, pp. 115-159, Plenum Press, New York (1975)] have been performed. The fact that bullatacin is active to both these cell lines to $10^{-12}$-$10^{-13}$ mcg/ml while bullatacinone is $5 \times 10^{-12}$ mcg/ml to human colon adenocarcinoma and $10^{-3}$ mcg/ml to human lung carcinoma suggested that bullatacinone has more selective cytotoxicities than bullatacin. Only a 7% displacement in a protein kinase C test at a concentration of 10 μM proved that bullatacin is not a phorbol ligand. A negative result in the protein tyrosine kinase test excluded its possible mechanism of action on protein tyrosine kinase. The mode of action for the acetogenins is still unknown, but it is postulated to involve cell membranes.

To test further the selective specificity of antitumor activities, bullatacin was sent to the NIH, NCI at Bethesda, Md., for their human tumor cell line panel tests including leukemia, non-small cell lung cancer, small cell lung cancer, colon cancer, breast cancer, CNS cancer melanoma, ovarian cancer, and renal cancer. These cytotoxicity results are shown in Table 6, where IC50 is the concentration of the compound that was found to cause 50% inhibition of the growth of each cell line listed under "Cell". IC90 is the concentration of compound that was found to cause 90% inhibition of the growth of each cell line. From the results, we can say that bullatacin is best active for certain CNS cancers, non-small cell lung cancers, leukemias, and ovarian cancers.

The substantially pure compounds in accordance with this invention can be formulated into dosage forms using pharmaceutically acceptable carriers for oral or parenteral administration to patients in need of oncolytic therapy. Preferred dose levels will depend on the attending physician's assessment of both the nature of the patient's particular cancerous condition and the overall physical condition of the patient. Effective antitumor doses of the present compounds may range from about 1 microgram per kilogram to about 200 micrograms per kilogram of patient body weight, more preferably between about 2 micrograms to about 100 micrograms per kilogram of patient body weight.

TABLE 6

NCI Developmental Therapeutical Program
In Vitro Testing Results for bullatacin (1)

| DISEASE | CELL LINE | IC$_{50}$(μg/ml) | IC$_{90}$(μg/ml) |
|---|---|---|---|
| Leukemia | HOLT-4 | $1.41 \times 10^\circ$ | $4.72 \times 10^\circ$ |
| | HL-60 TB | $<9.26 \times 10^{-4}$ | — |
| | K562 | $<9.26 \times 10^{-4}$ | $4.5 \times 10^\circ$ |
| | P388/ADR | $<9.26 \times 10^{-4}$ | $2.56 \times 10^\circ$ |
| | CCRF-CEM | $8.94 \times 10^{-5}$ | $6.94 \times 10^{-2}$ |
| | P388 | $>9.24 \times 10^{-2}$ | $>9.24 \times 10^{-2}$ |
| Non-Small Cell Lung Cancer | H522 | $2.46 \times 10^\circ$ | $>9.24 \times 10^\circ$ |
| | H125 | $2.40 \times 10^\circ$ | $>9.26 \times 10^\circ$ |
| | H23 | $2.38 \times 10^\circ$ | $9.21 \times 10^\circ$ |
| | H460 | $2.87 \times 10^{-5}$ | $1.85 \times 10^{-4}$ |
| | H322 | $<9.26 \times 10^{-4}$ | $>9.26 \times 10^\circ$ |
| | EKV-X | $1.15 \times 10^{-4}$ | $>9.26 \times 10^{-2}$ |
| | HOP-62 | $<9.26 \times 10^{-4}$ | $5.13 \times 10^\circ$ |
| | SK-MES-1 | $>9.24 \times 10^{-2}$ | $>9.24 \times 10^{-2}$ |
| | A-549(ATCC) | $5.04 \times 10$ | $>9.24 \times 10^{-2}$ |
| Small Cell Lung Cancer | H82 | $1.99 \times 10^\circ$ | $7.14 \times 10^\circ$ |
| | H524 | $2.69 \times 10^\circ$ | $7.54 \times 10^\circ$ |
| | H69 | $2.44 \times 10^\circ$ | $7.52 \times 10^\circ$ |
| | H146 | $6.75 \times 10$ | $>9.26 \times 10^\circ$ |
| Colon Cancer | SW620 | $5.64 \times 10^{-3}$ | $5.66 \times 10^\circ$ |
| | LOVO | $9.15 \times 10^{-4}$ | $4.69 \times 10^\circ$ |
| | DLD-1 | $2.76 \times 10^\circ$ | $8.62 \times 10^\circ$ |
| | HCC-2998 | $4.05 \times 10^\circ$ | $>9.26 \times 10$ |
| | HT29 | $3.84 \times 10^{-3}$ | $>9.24 \times 10^{-2}$ |
| Breast Cancer | MCF7 | $>9.24 \times 10^{-2}$ | $>9.24 \times 10^{-2}$ |
| CNS Cancer | TE-671 | $2.56 \times 10^{-5}$ | $2.74 \times 10^{-3}$ |
| | U251 | $<9.24 \times 10^{-6}$ | $4.37 \times 10^{-5}$ |
| | SNB-19 | $>9.26 \times 10^{-1}$ | $>9.26 \times 10^{-1}$ |
| | SNB-44 | $4.42 \times 10^\circ$ | $>9.26 \times 10^\circ$ |
| | SNB-75 | $3.35 \times 10^\circ$ | $>9.26 \times 10^\circ$ |
| Melanoma | SK-MEL5 | $>9.26 \times 10^{-4}$ | $5.22 \times 10^\circ$ |
| | RPMI-7951 | $2.73 \times 10^\circ$ | $7.71 \times 10^\circ$ |
| | MALME-3M | $2.82 \times 10^\circ$ | $7.67 \times 10^\circ$ |
| | LOX | $<9.26 \times 10^{-4}$ | $3.76 \times 10^\circ$ |
| | SK-MEL2 | $3.25 \times 10$ | $8.64 \times 10^\circ$ |
| Ovarian Cancer | A2780 | $3.77 \times 10^{-5}$ | $6.50 \times 10^{-4}$ |
| | OVCAR-8 | $2.57 \times 10^\circ$ | $7.65 \times 10^\circ$ |
| | OVCAR-5 | $8.80 \times 10^\circ$ | $>9.26 \times 10^\circ$ |
| | OVCAR-4 | $>9.24 \times 10^{-2}$ | $>9.24 \times 10^{-2}$ |
| | OVCAR-3 | $>9.24 \times 10^{-2}$ | $>9.24 \times 10^{-2}$ |
| Renal Cancer | A498 | $4.24 \times 10^{-5}$ | $3.71 \times 10^{-3}$ |
| | A704 | $1.36 \times 10^\circ$ | $8.00 \times 10^\circ$ |
| | SN12-K1 | $2.24 \times 10^{-5}$ | $2.87 \times 10^{-4}$ |
| | UO-31 | $1.94 \times 10^\circ$ | $>9.26 \times 10^\circ$ |
| | CAKI-1 | $3.94 \times 10^{-3}$ | $>9.24 \times 10^{-2}$ |

B. Pesticidal Activity

Pesticidal bioassays on initial fractions were conducted at Eli Lilly Laboratories (Greenfield, Ind.) following standard procedures with seven indicator organisms: mosquito larvae (ML), blow fly larvae (BFL), corn root worm (CRW), two-spotted spider mite (2SSM), southern army worm (SAW), melon aphid (MA), and *Haemonchus contortus* (HC). Results in Table 7 showed unusually high activity for F005 on ML, 2SSM, MA, and BFL. This suggested that F005, itself could be used as a potent pesticidal agent.

The pesticidal activities of bullatacin (1) and bullatacinone (2) are shown in Table 7 A. The results indicate that bullatacin is significantly toxic to cotton aphids (CA) at 1 ppm, southern corn rootworm (CRW) at 24 ppm, and two-spotted spider mites (2SSM) at 10 ppm. The compounds can be formulated at concentrations of about 1 to about 200 ppm in conventional liquid or solid forms for application to pest infected areas. The lack of pesticidal activity for bullatacinone indicates that it did not contribute to the pesticidal activities of the initial ethanol extract.

It is understood that the foregoing detailed description is given merely by way of illustration and that modification and variation may be made therein without departing from the spirit and scope of the invention.

What is claimed:

1. A compound selected from the group consisting of bullatacin and bullatacinone, characterized by the formulae

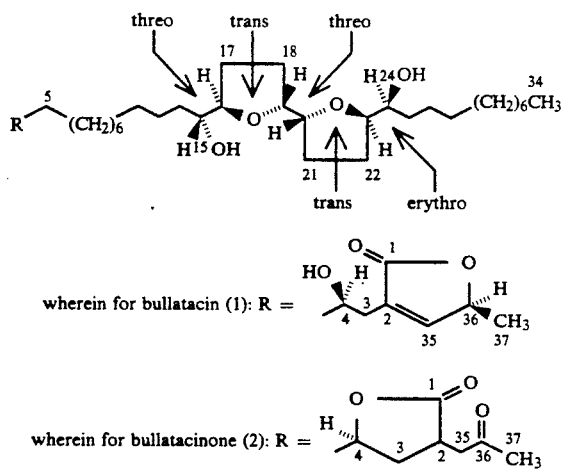

in substantially pure form, dihydrobullatacin, the corresponding peracetylated derivatives of bullatacin, dihydrobullatacin and bullatacinone, and mixtures of bulllatacin and bullatacinone in substantially pure form.

2. The substantially pure compound bullatacin in accordance with claim 1.

3. The substantially pure compound bullatacinone in accordance with in claim 1.

4. A chemotherapeutic composition for treatment of cancer comprising a substantially pure compound selected from the group consisting of bullatacin, dihydrobullatacin, bullatacinone and their peracetylated derivatives, in an amount effective to promote remission of said cancer, in a pharmaceutically acceptable carrier therefor.

5. The composition in accordance with in claim 4 wherein said compound is bullatacin.

6. The composition in accordance with in claim 4 wherein said compound is bullatacinone.

7. The composition in accordance with claim 4 wherein said compound is selected from the group consisting of dihydrobullatacin and the peracetylated derivatives of bullatacin, dihydrobullatacin and bullatacinone.

8. A substantially pure compound of the formula

TABLE 7

Pesticidal activities of inital fractions

| | PLEX (% MORTALITY) | | | | | MIS (% MORTALITY) | | | ACTIVITY | |
|---|---|---|---|---|---|---|---|---|---|---|
| | ML | | | BFL | HC | CRW | SAW | 2SSM | MA | | |
| | 100 ppm | 10 ppm | 1 ppm | 1% | 0.1% | 300 | 5000 | 5000 | 5000 | PLEX | MIS |
| F001 | 100 | 100 | 100 | 100 | 0 | 0 | 0 | 0 | 0 | A | N |
| F002 | 0 | 0 | 0 | 0 | 0 | 0 | 0 | 0 | 0 | A | N |
| F003 | 100 | 100 | 100 | 100 | 0 | 0 | 0 | 90 | 90 | A | A |
| F004 | 100 | 0 | 0 | 0 | 0 | 0 | 0 | 0 | 0 | A | N |
| F005 | 100 | 100 | 100 | 100 | 0 | 0 | 0 | 80 | 80 | A | A |
| F006 | 100 | 0 | 0 | 0 | 0 | 0 | 0 | 70 | 80 | A | A |

TABLE 7A

Pesticidal activities of 1 and 2.[a]

| Compound | ppm | Pest/percent control | | | | |
|---|---|---|---|---|---|---|
| | | CA | ML | SAW | CRW | 2SSM |
| Bullatacin(1) | 0.5 | —[b] | 0 | — | — | — |
| | 1 | 80 | 0 | — | — | — |
| | 6 | — | — | — | 20 | — |
| | 10 | 80 | 80 | 0 | — | 20 |
| | 24 | — | — | — | 80 | — |
| | 100 | 80 | — | 0 | — | 30 |
| | 400 | 90 | — | 0 | — | 20 |
| Bullatacinone (2) | 0.5 | — | 0 | — | — | — |
| | 1 | — | 0 | — | — | — |
| | 6 | — | — | — | 0 | — |
| | 10 | 0 | 0 | 0 | — | 0 |
| | 24 | — | — | — | 0 | — |
| | 100 | 0 | — | 0 | — | 0 |
| | 400 | 0 | — | 0 | — | 0 |

[a] See pesticidal activity section for details and definitions of abbreviation.
[b] A dash (-) indicates that tests were not conducted.

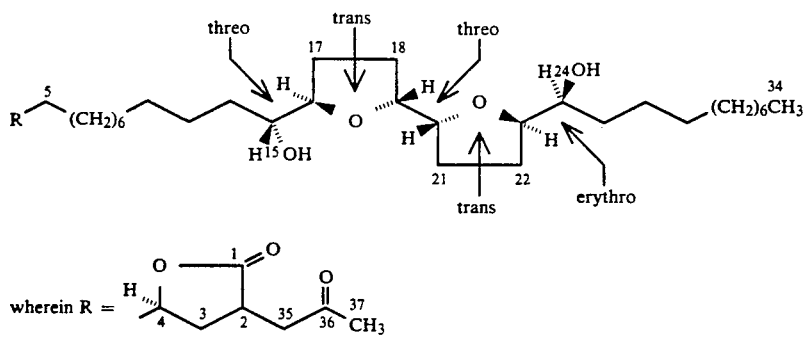
and its diacetate.
9. A chemotherapeutic composition for treatment of cancer comprising a substantially pure compound selected from the group consisting of bullatacinone and bullatacinone diacetate in an amount effective to promote remission of said cancer, in a pharmaceutically acceptable carrier therefor.
* * * * *